United States Patent [19]
Arnette

[11] Patent Number: 5,809,580
[45] Date of Patent: Sep. 22, 1998

[54] MULTI-SPORT GOGGLE WITH INTERCHANGEABLE STRAP AND TEAR-OFF LENS SYSTEM

[75] Inventor: Gregory F. Arnette, Monarch Beach, Calif.

[73] Assignee: Bausch & Lomb Incorporated, Rochester, N.Y.

[21] Appl. No.: 770,976

[22] Filed: Dec. 20, 1996

[51] Int. Cl.[6] ............................ A42B 7/00; A61F 9/02
[52] U.S. Cl. ...................................... 2/426; 2/450
[58] Field of Search ............................. 2/426, 431, 434,
2/438, 439, 441, 442, 443, 447, 452, 454,
450, 10, 15, 262; 351/41, 63; 16/228; 128/207.11;
D16/311

[56] References Cited

U.S. PATENT DOCUMENTS

| | | | |
|---|---|---|---|
| H1023 | 3/1992 | Wiseman | 2/438 |
| D. 292,329 | 10/1987 | Vitaloni | D29/9 |
| D. 324,745 | 3/1992 | Flores | D29/9 |
| D. 351,850 | 10/1994 | Bolle | D16/304 |
| D. 359,502 | 6/1995 | Hicks | D16/311 |
| D. 368,107 | 3/1996 | Lutz et al. | D16/311 |
| D. 372,928 | 8/1996 | Brune et al. | D16/311 |
| 2,406,608 | 8/1946 | Joyce | 2/14 |
| 3,896,496 | 7/1975 | Leblanc | 2/14 |
| 3,945,044 | 3/1976 | McGee et al. | 2/14 |
| 4,076,373 | 2/1978 | Moretti | 350/61 |
| 4,138,746 | 2/1979 | Bergmann | 2/434 X |
| 4,428,081 | 1/1984 | Smith | 2/438 |
| 4,455,689 | 6/1984 | Boyer | 2/434 |
| 4,563,065 | 1/1986 | Kreissl | 351/86 |
| 4,716,601 | 1/1988 | McNeal | 2/434 |
| 4,748,697 | 6/1988 | Hodnett | 2/438 |
| 4,977,627 | 12/1990 | Metcalfe et al. | 2/437 |
| 5,213,241 | 5/1993 | Dewar et al. | 224/222 |
| 5,592,698 | 1/1997 | Woods | 2/434 X |

*Primary Examiner*—C. D. Crowder
*Assistant Examiner*—Shirra L. Jenkins
*Attorney, Agent, or Firm*—Katherine McGuire; Craig E. Larson

[57] ABSTRACT

A multi-sport goggle having a tear-away lens system includes a pair of strap brackets which pivotally and removably attach a goggle strap to the goggle frame. One of the strap brackets includes a third post to removably secure the lateral pull-strap of the tear-away lenses, the other two posts (for securing the panes of the tear-away lenses over the permanent lens) being carried on a pair of lens brackets which are removably secured to either side extent of the goggle frame.

16 Claims, 4 Drawing Sheets

MULTI-SPORT GOGGLE WITH INTERCHANGEABLE STRAP AND TEAR-OFF LENS SYSTEM

BACKGROUND OF THE INVENTION

The present invention relates to goggles primarily intended for use in sports. The invention more particularly relates to a goggle which includes interchangeable head and helmet straps and an optional tear-away lens system to selectively accommodate a variety of sports and attendant environmental conditions.

Goggles are used in a wide variety of sports to protect the face, some examples of which include skiing, snowboarding, biking, and motocross. The environmental conditions are usually different depending on the sport and, as such, the type of goggle used varies in accordance with the type of environmental conditions expected to be present during the particular sporting activity. During skiing and snowboarding, for example, a goggle is selected which is resistant to moisture accumulating inside the lens cavity which could fog the lens and thereby decrease the skier's visibility. During biking and motocross, the exterior surface of the lens of a goggle is subject to excessive accumulation of dirt and mud which quickly diminishes the wearer's view therethrough. One successful solution to this problem is the tear-away, disposable lens which provides a stack of flexible plastic transparencies or lenses which are cut in the general shape as and positioned over the more rigid, permanent lens. Means are provided to quickly and successively tear away the outer-most lens as it becomes dirty, thereby exposing a clean lens as needed. Examples of this type of lens system may be seen in the following U.S. Pat. Nos. 4,076,373 issued to E. D. Bullard Company on Feb. 28, 1978 (Discloses roller-type rather than tear-away lens system) No. 4,455,689 issued to Boyer on Jun. 26, 1984 No. 4,563,065 issued to Optyl Eyewear on Jan. 7, 1986 No. 4,716,601 issued to McNeal on Jan. 5, 1988

While the tear-away lens system is useful in a goggle for use in sports where the lens is likely to become constantly dirty (e.g., motocross), this type of lens system is neither necessary nor desirable in other environmental conditions such as those expected during skiing and snowboarding, for example. It would therefore be beneficial to be able to selectively adapt a goggle to these different environmental conditions such that a wearer need only a single goggle for a variety of different sports and their associated environmental conditions.

In addition to the above concern regarding the lens of the goggle, the strap which secures the goggle to the face may also have different characteristics according to the goggle's intended use. For example, in sports where a helmet is commonly used (e.g., motocross), it is desirable to have an additional, high-friction material applied to the inner surface of the elastic strap (e.g., silicone) to ensure firm placement of the strap about the helmet. Conversely, when no helmet is worn (e.g., during skiing), the high friction material is not needed and a strap lacking this feature would be used. It would therefore be beneficial to be able to interchange different straps intended for different sports, or simply having different colors, upon the same goggle in a quick and efficient manner.

Lastly, the fit of the goggle on the face is always a concern, it being very desirable to have the periphery of the goggle conform and provide a sealing yet comfortable fit to the face.

SUMMARY OF THE INVENTION

The present invention addresses the above needs by providing a goggle which may be selectively adapted for use in a variety of different sport conditions. The goggle of the present invention is particularly adaptable for selective use in winter conditions on the one hand (e.g., during skiing and snowboarding), and excessive dirt and mud conditions on the other hand (e.g., during motocross).

The goggle includes a molded plastic goggle frame which is semi-rigid and includes venting passages and a foam backing for placement against the face in the usual construction of face goggles. A pair of lens brackets for the disposable lens stack are removably attached to either side of the frame with portions of the brackets extending over the outer surface of the permanent lens whose periphery extends within a groove formed along the inside edge of the top and bottom extents of the goggle frame. The tear-away lens system includes a stack of plastic lenses cut in the general shape as the permanent (and harder) plastic lens on the goggle. It is preferable, although not necessary, that the so-called permanent lens itself be interchangeable on the goggle frame.

The portions of the brackets which extend over the permanent lens each include a knobbed post over which a respective pair of holes formed in the stack of tear-away lenses are aligned and passed such that the stack lies in covering relation over the permanent lens. An integrally formed pull-strap extends from the same side of each lens in the stack which is manually grasped and pulled to tear the outermost, dirty lens from the goggle.

Means are provided to enable selective and quick interchange between straps having different colors and/or straps having different features (e.g., a strap intended for use with a helmet would have a high friction material affixed to the interior surface of the strap whereas a strap intended for use directly against the head would not). The selective strap-interchange means comprises a pair of rigid strap brackets which are of generally rectangular configuration. An end of the strap is attached to one side of the bracket while the opposite side of the bracket, which extends parallel to the side to which the strap attaches, pivotally and removably connects to a side of the goggle frame adjacent to the lens bracket. A strap bracket is connected to each side of the goggle with an elongated post member which extends through a pair of vertically spaced holes formed in each side of the goggle frame, and an elongated hole formed in the side of the strap bracket which extends between and is aligned with the spaced holes in the goggle frame.

The elongated post members each include a rounded tip at one end thereof, and a radial projection at the opposite end thereof. With the elongated hole of the strap bracket aligned between the vertically spaced holes in the goggle frame, the rounded tip of the elongated post member is directed consecutively therethrough until it reaches the bottom-most hole in the goggle frame. This hole has a diameter slightly smaller than the diameter of the rounded tip and, as such, the rounded tip may be press-fit through this hole, thereby securing the post member, and thus also the strap-securing member, to the goggle frame. The opposite end of the post is counter-sunk in the upper-most hole of the goggle frame with the projection thereof lying in a small channel which extends radially from the upper-most hole to the edge of the goggle frame. The projection is accessible with a finger or thumb of the wearer to remove the post from the goggle frame which thereby also releases the strap bracket from the goggle frame for replacement with a different strap as desired.

DETAILED DESCRIPTION

Figure 1:
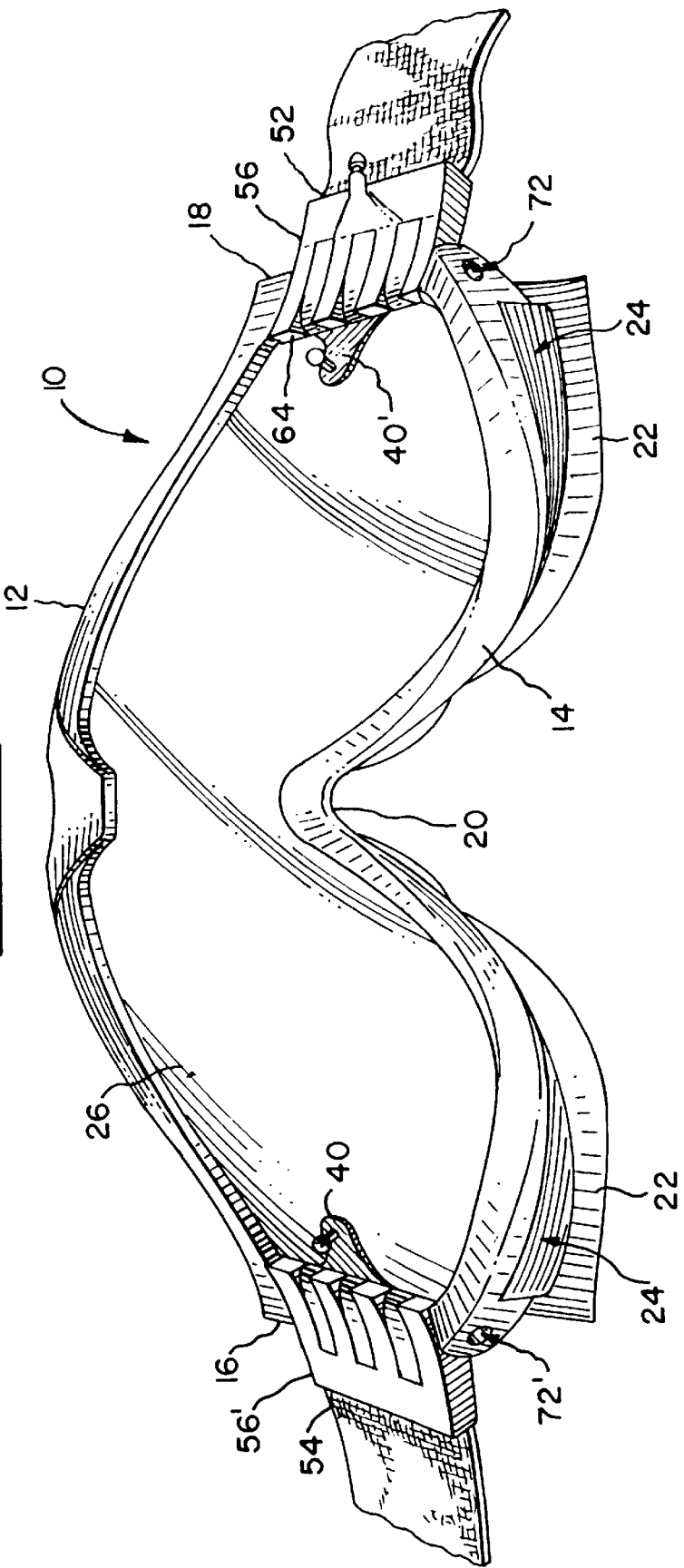
FIG. 1 is a top, perspective view of the goggle frame, absent any lens, and including the lens brackets and the strap brackets on either side of the frame.

Referring to the drawing, there is seen in the figures a goggle frame 10 which includes a top extent 12, a bottom extent 14, and opposite side extents 16 and 18. Preferably, the top and bottom extents or edges are positioned or spaced laterally outwardly of the side extents or edges Bottom extent 14 includes a central indentation 20 which is placed over the nose of the wearer, although it is understood the goggle could also be of the type which fits over the nose of the wearer. Goggle frame 10 is molded from a semi-rigid plastic material (e.g., vinyl) which includes enough flexibility to conform comfortably to the face of the wearer, yet provides enough rigidity to prevent distortion of a lens mounted thereon. In this regard, a flexible boot 22 is fixed about the perimeter of the interior surface of the goggle frame which is of a softer durometer material than frame 12 since boot 22 is the part of the goggle which comes into direct and sealing contact with the face. Venting passages 24, which may be covered with a permeable foam material, for example, are provided along the top (not shown) and bottom of the goggle frame 12 to keep moisture and debris from accumulating in the lens cavity.

Figure 3:
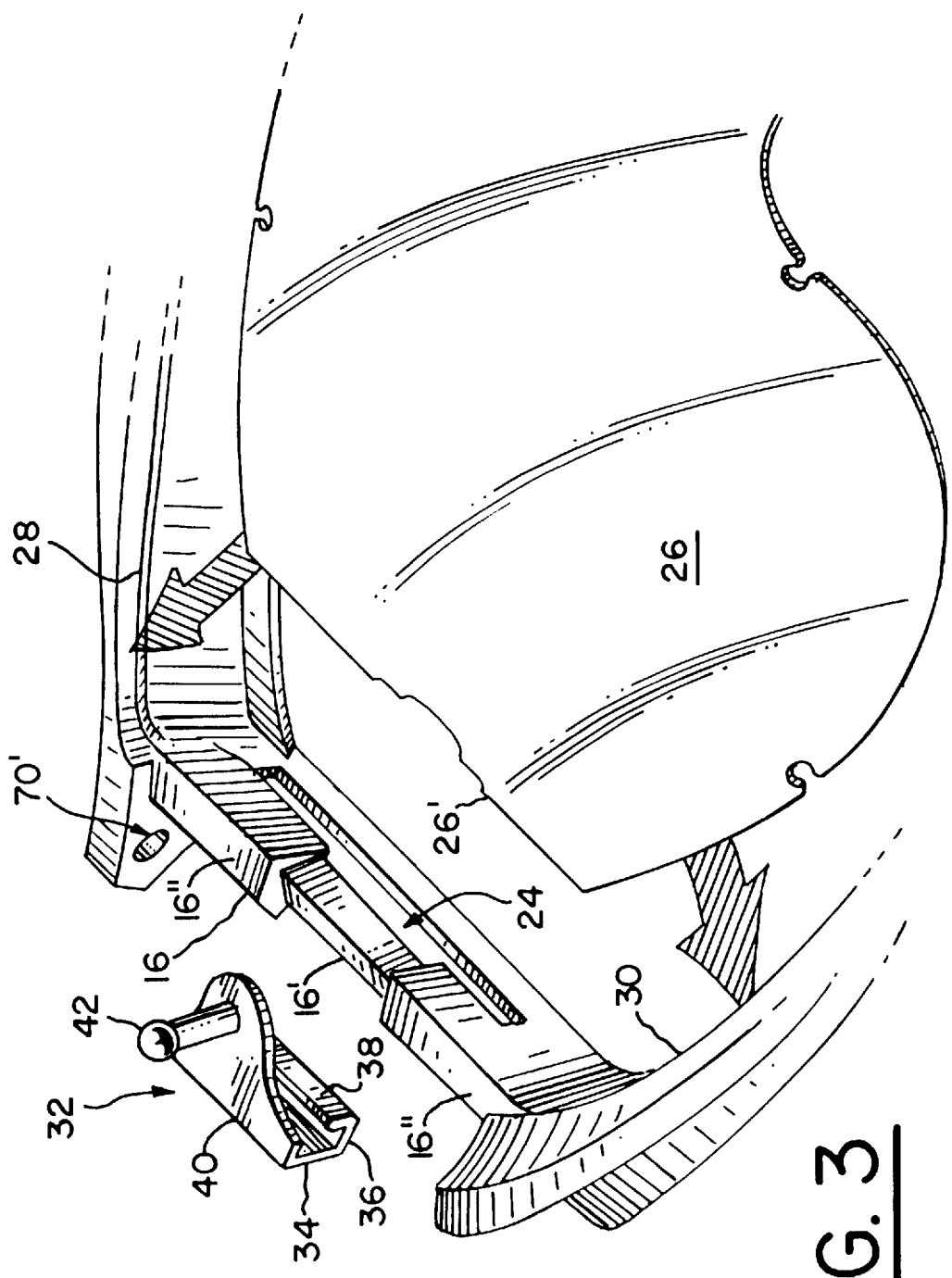
FIG. 3 is a fragmented, perspective view of one side of the goggle frame with a lens bracket spaced therefrom, and further showing the manner of securing the permanent lens (also fragmented) on the frame.

As seen best in FIG. 3, a "permanent" lens 26 having opposite side edges, is provided which fits within grooves 28,30 formed along the top and bottom frame extents 12,14, respectively. Lens 26 is described as a "permanent" lens herein to differentiate it from the stack of disposable lenses to be described; however, it is understood lens 26 may itself be replaced upon frame 10 as desired.

An optional tear-away lens system is provided on goggle 10 as follows. A pair of lens brackets 32,32' are provided which may be removably attached to either side extent 16,18 of frame 10, respectively. More particularly, lens brackets 32,32' are each configured with two wall portions 34,34' and 36,36' which extend at substantially right angles to each other; a flange portion 38,38' which traverses the edge of wall portion 36,36' located opposite wall portion 34,34'; and a top wall portion 40,40' which extends angularly from the edge of wall portion 34,34' located opposite wall portion 36,36'. Side extents 16,18 of frame 10 each include areas of reduced cross-section 16', 18' where lens brackets 32,32' may be removably secured by press-fitting areas 16', 18' between wall portions 34,34' and flanges 38,38', respectively. It is noted permanent lens 26 is first placed into the frame 10 as described above, with the side edges 26' of the lens 26 lying over the outwardly facing surfaces 16",18" of side extents 16,18. Once lens 26 is in place on frame 10, brackets 32,32' are secured to areas 16',18' as described, with top wall portions 40,40' extending over lens 26 as seen best in FIG. 1.

Each top wall portion 40,40' of each lens bracket 32,32' includes a knobbed post 42,42' extending therefrom. A plurality of stacked, disposable lenses 44 (FIG. 2) is provided, each having a front pane which is cut in the general shape of permanent lens 26, and a laterally extending, integral pull-strap 45'. Each lens 44 further includes a first pair of holes 46,48 at the opposite ends of the front pane which may be aligned with and passed over knobbed posts 42,42', thereby removably securing the stack of lenses 44 over permanent lens 26. The lateral pull-straps are secured to one side of the goggle frame 10, in the manner described below, such that the wearer can successively pull at the outer-most strap 45', lifting the outer-most lens 44 off of posts 42,42' and thereby revealing a clean lens therebeneath as needed.

Turning attention to the interchangeable goggle strap, an elastic goggle strap 50 is provided having opposite first and second end portions 52,54, respectively. Although not shown, one or more buckles may be attached to strap 50 to provide length adjustment. In this regard, strap 50 may actually consist of more than one separate length of material, joined by the buckles. Means to removably attach strap 50 to goggle frame 10 are provided in the form of a pair of strap brackets 56,56' which are of generally rectangular configuration, having top, bottom, and first and second opposite side edges 60,62,66,64, respectively, and opposite outwardly and inwardly facing surfaces 65, 67, respectively. As seen best in FIG. 4, first side edge 66 of each strap bracket 56,56' is slotted such that the end 52 of strap 50 may be passed therethrough to secure the strap to the strap bracket. Furthermore, the end 52 of strap 50 may be stitched back upon itself to substantially prevent the strap edge from accidentally backing out of the slot and releasing from the strap bracket, although it is intended that the strap may be forced manually back through the slot should it be desired to replace a worn strap on the strap bracket.

As mentioned above, means are provided for removably, pivotally attaching the strap brackets, and thus also strap 50, to the goggle frame 10. In particular, each strap bracket further includes an elongated hole 68 which extends entirely therethrough adjacent and parallel to side edge 64 thereof. This hole 68 may be aligned with a pair of vertically spaced holes 70,72 formed in the top and bottom extents 12,14 which extend slightly laterally beyond side edges 16,18 of goggle frame 10. In this regard, it is noted the length of side edge 64 of the strap bracket is slightly smaller than the distance "D" between the top and bottom extents 12,14 at holes 70,72. With side edge 64 thus inserted between top and bottom extents 12,14 of goggle frame 10, and with hole 68 in strap bracket 56 aligned with vertically spaced holes 70,72 in the goggle frame, an elongated post member 74 having first and second opposite is passed therethrough, thereby pivotally securing the strap bracket 56 to the goggle frame. (Although not shown in the drawing, a post identical to post 74 is provided to secure strap bracket 56' to the opposite side of goggle frame 10 in the same manner).

More particularly, post 74 is snap-fit into hole 72 which has a diameter slightly smaller than the first rounded bottom end 76 of post 74. The second top end of post 74 is provided with a radial projection 78. In the fully inserted condition of post 74 in holes 70, 68 and 72, the top end of post 74 is counter-sunk in hole 70 with radial projection 78 lying in a channel 71 which extends radially from hole 70 in top extent 12. To remove post 74, the wearer simply uses a finger or thumb to lift the radial projection 78, and thus the post 74 from the frame 10, thereby releasing the strap bracket 56 from the goggle frame. As such, a different strap 50 attached to the same or different strap brackets 56,56' may be attached to the goggle frame 10. The strap may simply be of a different color, or it may have different characteristics or features (e.g., silicone applied to the interior surface thereof) as desired. It will be appreciated post 74 provides a quick and easy means by which to interchange different straps upon goggle frame 10. Additionally, the pivot action of strap brackets 56,56' enable strap 50 to conform to a variety of head and helmet sizes while ensuring a snug fit of the goggle on the face. The location of the pivot post 74 closely adjacent the edge of the lens 26 contributes to this optimized fitting action of the strap and goggle on the face.

Figure 2:
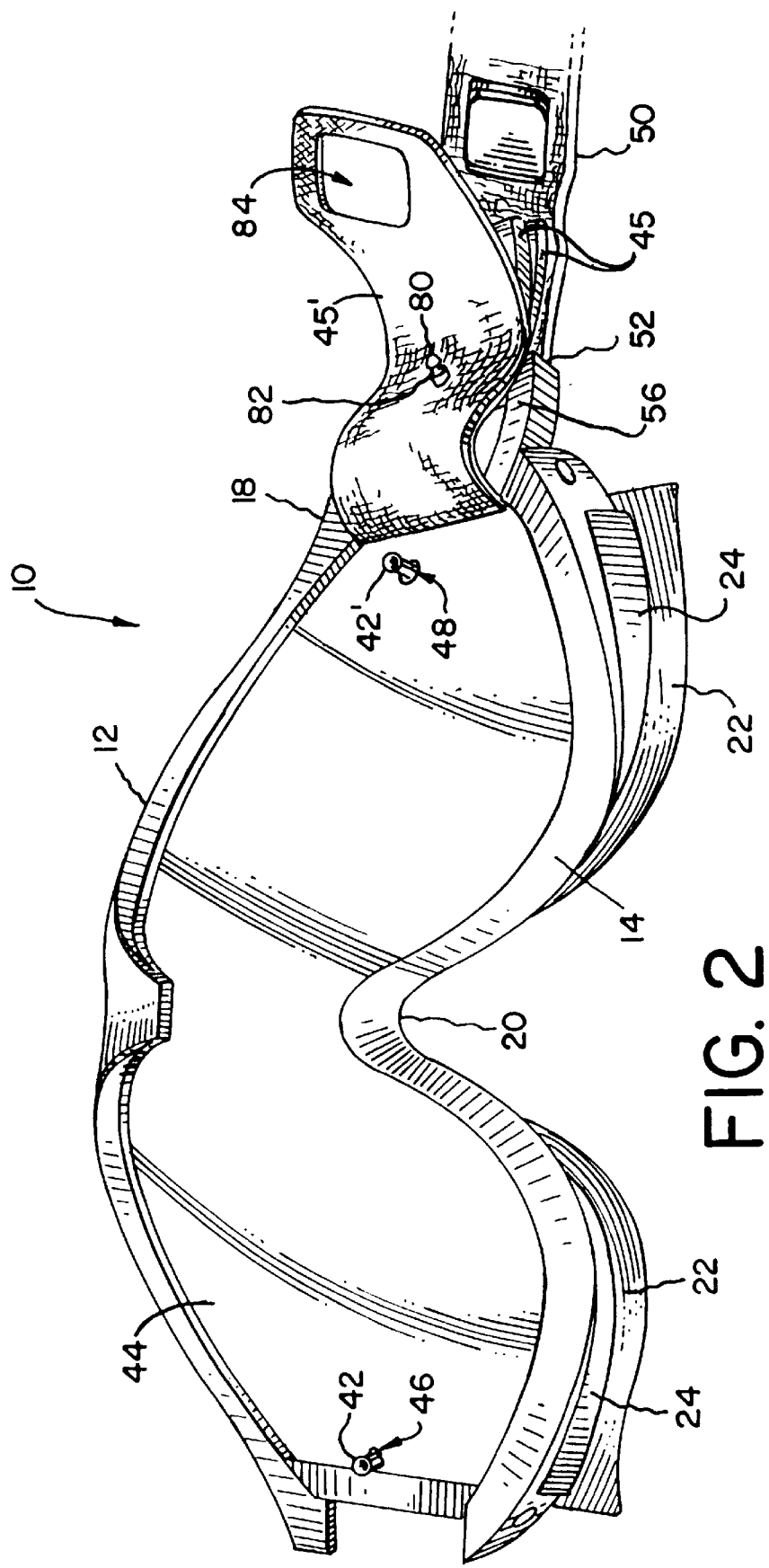
FIG. 2 is the view of FIG. 1 and further showing a tear-away lens stack mounted on the frame against the permanent lens.
Figure 4:
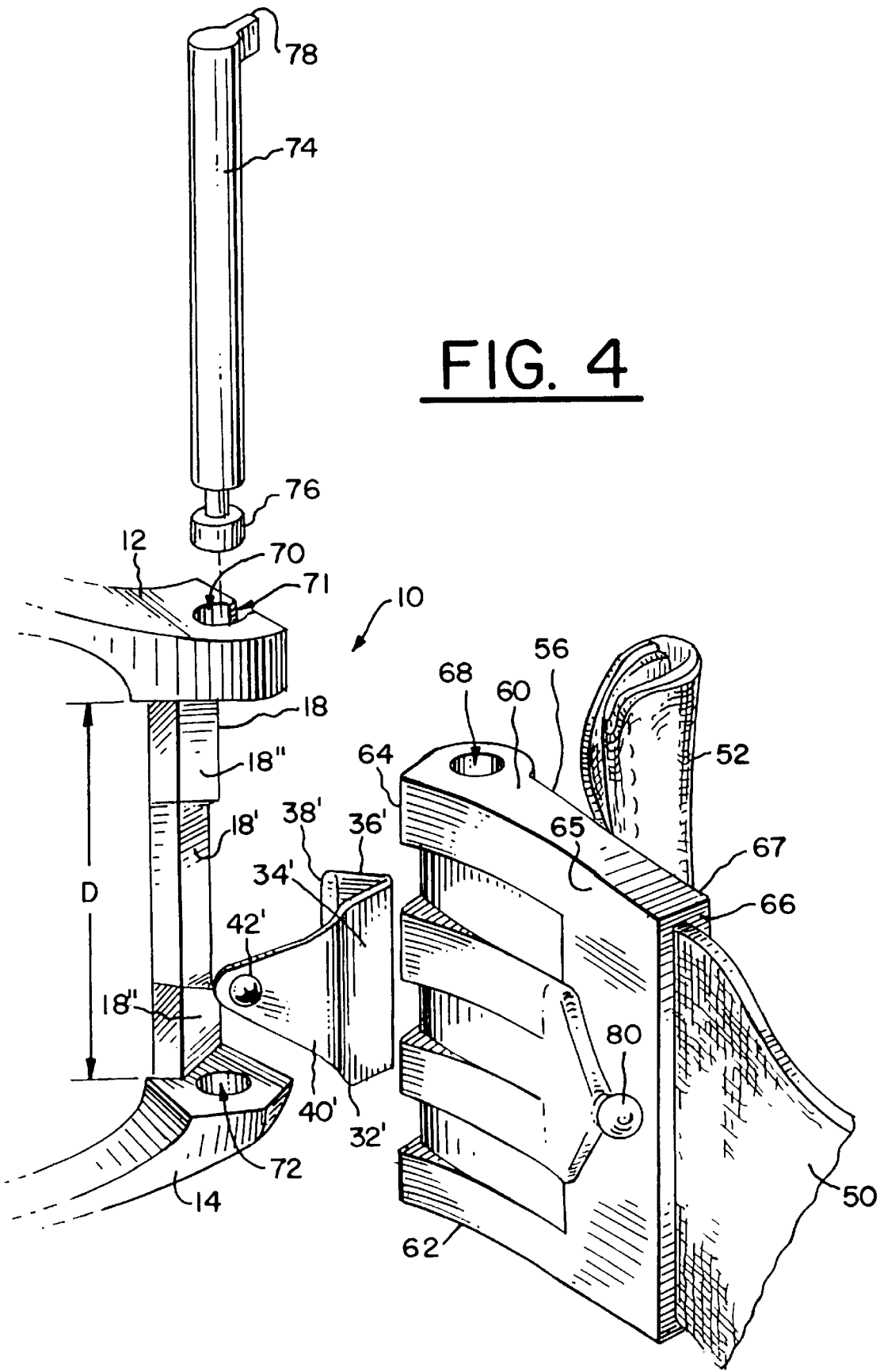
FIG. 4 is a perspective, assembly view of one side of the goggle frame including its post member, strap-securing bracket and lens-securing bracket.

Referring still to FIG. 4, and now also back to FIG. 2, it will be seen that one of the strap brackets 56 includes a post 80 extending from the outwardly facing surface 65 thereof, opposite the inwardly facing surface 67 from which strap edge 52 exits slotted edge 66. Post 80 extends at an acute angle from bracket surface 65, extending in the direction toward edge 66 (which is in a direction laterally away from the goggle frame 10). Referring strictly to FIG. 2, the pull-strap 45' of each lens 44 includes a small hole 82 in approximately the center thereof, and a larger hole 84 adjacent the outer edge thereof. The small hole 82 of each lens 44 in the stack is passed over post 80 which is of a diameter slightly larger than the hole 82. The larger hole 84 is also passed over post 80 of each lens in the stack, working from the bottom up, with the outer-most strap remaining free such that it is accessible by the wearer to pull when needed. As a lens is pulled free from frame 10, the strap directly therebeneath unfolds such that it is then accessible to be pulled off of frame 10 when needed.

The present tear-away lens system thus provides a total of three posts 42,42' and 80 to which the lens stack is secured. Since the third post extends from the strap bracket which itself is pivotal on the frame, the post 80 is also pivotal on the frame.

As stated previously, a tear-away lens system is desirable in certain sports such as motocross where the lens constantly becomes covered with dirt and mud. Should the wearer want to use the goggle for a different sport where this is not a problem (e.g., skiing), the lens brackets 32,32' may be simply and quickly removed from frame 10 by prying them free of areas 16', 18'. Also, should the wearer desire to change strap 50 to a different type and/or color, strap brackets 56,56' may be removed from frame 10 by backing out posts 74 from either side of frame 10. There is thus provided a novel and unique multi-sport goggle which is quickly adaptable to the specific needs of the user.

What is claimed is:

1. Apparatus for attaching a strap having first and second ends on a goggle frame, said apparatus comprising:
    a) a strap bracket having first and second, opposite side edges, said strap first end attached to said first side edge of said strap bracket, said second side edge of said strap bracket including an elongated hole extending the full length of said second edge; and
    b) an elongated post having first and second, opposite ends, said elongated post being insertable through said elongated hole in said strap bracket and a pair of holes formed in said goggle frame and between which said second side edge of said strap bracket is positioned, whereby said elongated post removably and pivotally secures said strap bracket and said strap to said goggle frame.

2. The apparatus of claim 1 wherein said post includes a first end having a rounded end which is press-fit into one of said pair of holes formed in said goggle frame.

3. The apparatus of claim 2 wherein said post includes a second end having a radial projection which, in the fully inserted condition of said post on said frame, is accessible with a finger to lift said post free from said elongated hole in said strap bracket and said pair of holes in said frame, thereby releasing said strap bracket from said frame.

4. The apparatus of claim 1 wherein said goggle frame includes a goggle lens having opposite side edges, and wherein the point of pivotal attachment between said post and said frame is positioned laterally outwardly of a said side edge of said lens.

5. The apparatus of claim 1 wherein said goggle frame includes a top, bottom and opposite side extents, and wherein said pair of holes are formed in said top and bottom extents, respectively.

6. The apparatus of claim 5 wherein the portions of said top and bottom extents having said pair of holes extend laterally outwardly of an associated said side extent.

7. The apparatus of claim 6 wherein said goggle frame includes a lens having opposite side edges which abut said side extents of said frame, respectively.

8. The apparatus of claim 1, and further comprising a permanent goggle lens mounted in said goggle frame, said goggle lens having opposite side edges, and further comprising a tear-away lens system comprising a plurality of stacked, flexible lenses each including a front pane and a lateral pull-strap having at least one hole formed therethrough, and wherein said strap bracket includes an outwardly facing surface including a knobbed post extending therefrom, said stack of lenses being positionable over said permanent lens and said lateral pull strap of each said flexible lenses including a hole which may be passed over said knobbed post thereby removably securing said lateral pull strap of each said flexible lens to said strap bracket.

9. The apparatus of claim 8, and further including a means for removably securing said pane of each of said flexible lenses to said permanent lens.

10. The apparatus of claim 9 wherein said means comprises a pair of lens brackets removably attached to said side extents of said goggle frame, respectively, said lens brackets each including a knobbed post extending therefrom, said pane of each of said flexible lenses further including a pair of spaced holes which may be aligned with and removably passed over said knobbed posts on said lens brackets, respectively.

11. In a tear-off lens system for a goggle having a goggle frame with top, bottom and opposite side extents, a permanent lens having opposite side edges positionable therebetween, and a goggle strap, said tear-off lens system including a plurality of stacked, flexible lenses each having a front pane and a lateral pull-strap, said tear-off lens system further including at least one post attached adjacent one of said side extents of said goggle frame, said front panes of each of said flexible lenses including at least one hole which may be passed over said post to removably secure said panes in covering relation to said permanent lens, wherein the improvement comprises:
    a strap bracket having opposite outwardly and inwardly facing surfaces and first and second, opposite side edges, a first end of said goggle strap attached to said first side edge of said strap bracket, and further including a means for pivotally attaching said second side edge of said bracket to said goggle frame adjacent one of said side extents thereof, said strap bracket further including a post extending from said outwardly facing surface thereof, said lateral pull strap of each of said flexible lenses including at least one hole which may be passed over said post on said strap bracket, thereby removably securing said lateral pull-strap to said strap bracket.

12. In the tear-away lens system of claim 11, wherein said means comprises an elongated post which may be passed through a pair of spaced holes formed in said goggle frame, and an elongated hole formed in said second side edge of said strap bracket which extends between and aligns with said spaced holes in said goggle frame.

13. In the tear-away lens system of claim 12, wherein said spaced holes are formed in said top and bottom extents of said goggle frame adjacent a respective side extent thereof.

14. In the tear-away lens system of claim 13, wherein said elongated post includes a rounded end portion which is snap-fit into one of said spaced holes in said goggle frame.

15. In the tear-away lens system of claim 14, wherein said elongated post includes a radial projection at an end thereof opposite said rounded end portion, said radial projection being accessible with a finger in the fully inserted condition of said elongated post such that said elongated post may be lifted out of said spaced and elongated holes, thereby releasing said strap bracket from said frame.

16. In the tear-away lens system of claim 15, wherein the point of pivotal attachment of said strap bracket to said frame lies laterally outwardly adjacent to one of said side edges of said permanent lens.

* * * * *